US00PP24023P2

(12) United States Plant Patent
Kaneko

(10) Patent No.: US PP24,023 P2
(45) Date of Patent: Nov. 12, 2013

(54) ***ANEMONE* PLANT NAMED 'PKAN'**

(50) Latin Name: *Anemone×hybrida*
Varietal Denomination: PKAN

(76) Inventor: Katsunori Kaneko, Tokyo (JP)

( * ) Notice: Subject to any disclaimer, the term of this patent is extended or adjusted under 35 U.S.C. 154(b) by 136 days.

(21) Appl. No.: 13/385,220

(22) Filed: Feb. 7, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Penny J. Aguirre

(57) ABSTRACT

A new cultivar of hybrid *Anemone* named 'PKAN', characterized by its flowers that are upward facing, cup-shaped, and medium to deep pink in color, its numerous basal branches, and its dwarf plant habit.

2 Drawing Sheets

Botanical classification: *Anemone×hybrida.*
Cultivar designation: 'PKAN'.

BACKGROUND OF THE INVENTION

The present invention relates to a new and distinct cultivar of *Anemone×hybrida* known as 'PKAN' and is hereinafter referred to by the cultivar name 'PKAN'.

The new cultivar, 'PKAN', arose as a naturally occurring chimeral mutation of 'Chabo' (not patented). The Inventor discovered 'PKAN' in 2003 in a container at his nursery in Gero-she, Gifu, Japan.

Asexual reproduction of the new cultivar was first accomplished by the Inventor by root cuttings in Gero-she, Gifu, Japan in 2005. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'PKAN' as a new and unique cultivar of *Anemone.*

1. 'PKAN' exhibits flowers that are upward facing and cup-shaped.
2. 'PKAN' exhibits flowers that are medium to deep pink in color.
3. 'PKAN' exhibits numerous basal branches.
4. 'PKAN' exhibits a dwarf plant habit.

'PKAN' can be most closely be compared to its parent plant, 'Chabo'. 'PKAN' differs from 'Chabo' in having flowers that are darker pink in color and upright facing versus outward facing, in having more basal branching, and in having a more dwarf plant habit ('Chabo' reaches about 1 m in height).

'PKAN' can also be compared to the cultivars 'Pretty Lady Diana' (U.S. Plant Pat. No. 22,332) and 'Whirlwind' (not patented). 'Pretty Lady Diana' differs from 'PKAN' in being taller in height (about 50 cm) and 'Whirlwind' differs from 'PKAN' in being much taller in height (about 90 cm) and in having flowers that are about half the size and white in color.

BRIEF DESCRIPTION OF THE DRAWING

The accompanying colored photographs illustrate the overall appearance and distinct characteristics of the new *Anemone*. The photographs were taken of a plant about one year in age as grown in a 15-cm container in The Netherlands.

The photograph in FIG. 1 provides a side view of a typical plant habit of 'PKAN' in bloom.

Figure 1:
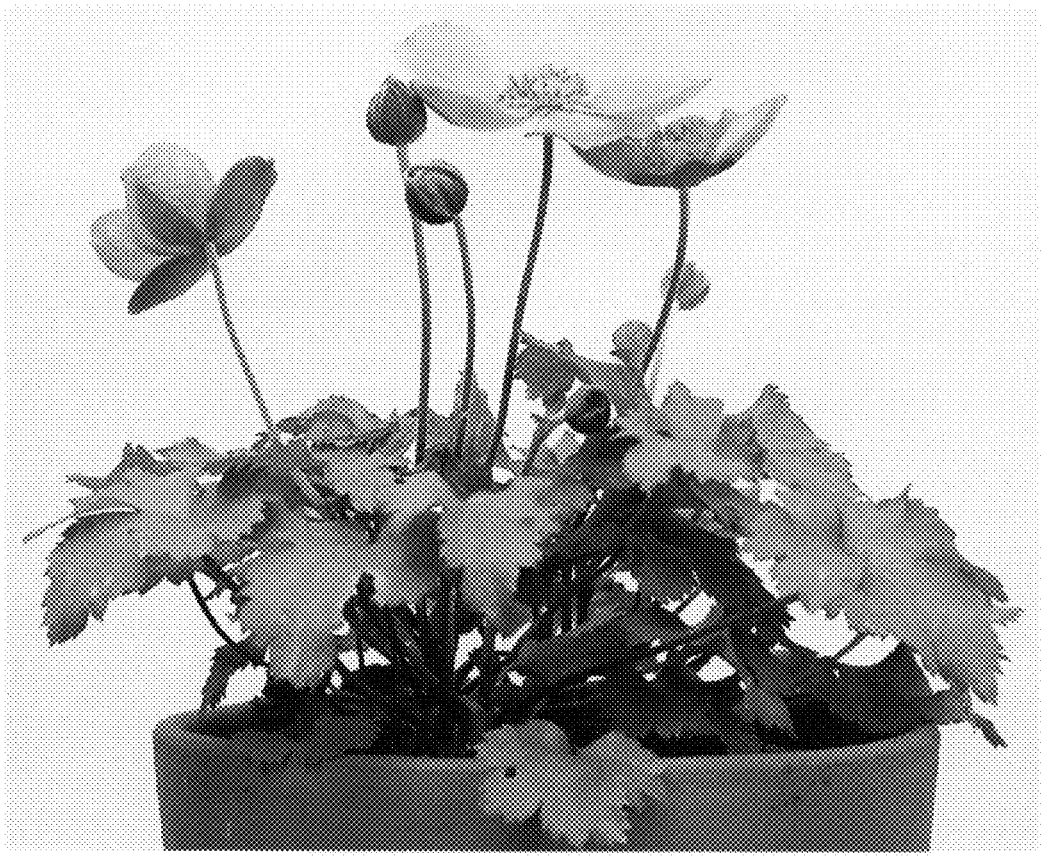
Figure 2:
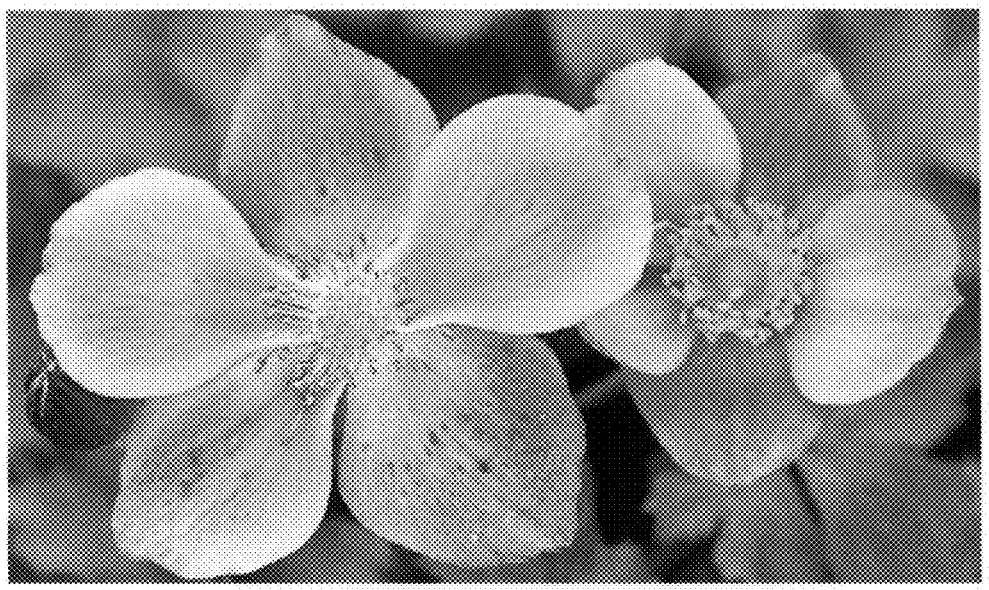

The photograph in FIG. 2 provides a close-up view of the flowers of 'PKAN'.

Figure 3:
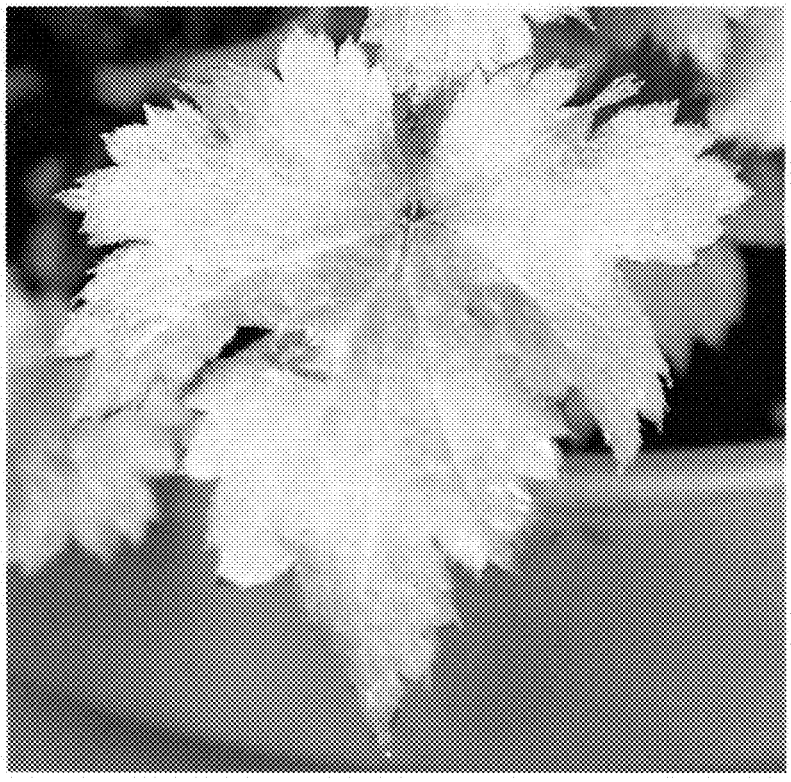

The photograph in FIG. 3 provides a close-up view of a leaf of 'PKAN'.

The colors in the photographs are as close as possible with the photographic and printing technology utilized. The color values cited in the detailed botanical description accurately describe the colors of the new *Anemone.*

DETAILED BOTANICAL DESCRIPTION OF THE PLANT

The following is a detailed description of one year-old plants of the new cultivar as grown in 15-cm containers outdoors in The Netherlands. Plants were grown under average day temperatures of 14° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Herbaceous perennial.
*Plant habit.*—Dwarf with dense basal branching.
*Height and spread.*—Reaches a height of about 14.8 cm in height and about 22.8 cm in width.
*Hardiness.*—At least in U.S.D.A. Zones 4.
*Diseases and pests.*—Not more susceptible to pests and diseases than other *Anemone* varieties.
*Root description.*—Fibrous.

*Branching habit.*—Basal rosettes of leaves with flowers growing from the center.

*Propagation.*—Root cuttings.

*Growth rate.*—Moderate.

Foliage description:

*Leaf shape.*—Broadly ovate.

*Leaf division.*—Simple.

*Leaf base.*—Hastate.

*Leaf apex.*—Acute.

*Leaf venation.*—Laciniate, color on upper surface; 146D and tinged with 176B, color on lower surface; 146B to 146C and tinged with 176B.

*Leaf margins.*—Lobed with an average number of 5 lobes, lobe margins serrate.

*Leaf attachment.*—Petiolate.

*Leaf arrangement.*—Basal rosettes.

*Leaf orientation.*—Held nearly horizontal to petiole.

*Leaf surface.*—Upper and lower surface; slightly glossy and sparsely covered with short adpressed hairs 0.5 mm in length and 157D in color.

*Leaf color.*—Young upper surface; 143A, young lower surface; 143C, mature upper surface; 143A, mature lower surface; 148B.

*Leaf size.*—Average of 5.3 cm in length and 4.9 cm in width.

*Leaf quantity.*—Average of 6 per rosette.

*Petioles.*—Average of 7.1 cm in length and 1 mm in diameter, 144A in color and flushed with a color between N186C and 200A (more strongly at base).

Flower description:

*Inflorescence type.*—None.

*Lastingness of flowers.*—About 7 days, self cleaning.

*Flower size.*—Average of 1.6 cm in height and 5.2 cm in diameter.

*Flower fragrance.*—Very faint, acidic-sweet.

*Flower arrangement.*—2 flowers per peduncle growing from the centers of the rosettes.

*Flower number.*—Average of 1 (occasionally 2) per rosette.

*Flower aspect.*—Upright to slightly outward.

*Flower bud.*—Globular in shape, average of 2 cm in length and 1 cm in diameter, color; a blend of N186C, 187A and 187B, base; 150B.

*Tepal number.*—Average of 5.

*Tepal shape.*—Broadly obovate to broadly elliptic.

*Tepal margin.*—Entire.

*Tepal size.*—Average of 3 cm in length and 2.4 cm in width.

*Tepal surface.*—Upper surface; smooth and moderately velvety, lower surface; pubescent with adpressed soft silky hairs, 2 mm in length and NN155C in color.

*Tepal apex.*—Rounded.

*Tepal color.*—When opening upper side; ranges from 64A to 64D, when opening under side; a blend of 59B and 64A to 64B, when fully opened upper side; 70A to 70B, when fully opened under side; 64A to 64B.

*Peduncle.*—Round in shape, 7.3 cm in length and 1.5 cm in diameter, a color between 144C and 145A and tinged with a color between N186C and 200A.

*Pedicel* .—None.

Reproductive organs:

*Gynoecium.*—Average of 60 pistils, 2 mm in length, style is 1 mm in length and 145A in color, ovary is 145A in color, stigma is club-shaped and 145A in color.

*Androcoecium.*—Average of 120 stamens; anthers are basifixed, kidney-shaped, 1.8 mm in length, and 14A in color, filaments are 8 cm in length and 157D in color, pollen very low in quantity and 14A in color.

*Fruit/seeds.*—No fruit or seeds detected to date.

It is claimed:

1. A new and distinct cultivar of *Anemone* plant named 'PKAN' as herein illustrated and described.

* * * * *